United States Patent [19]

Kamuro et al.

[11] Patent Number: 4,959,093

[45] Date of Patent: Sep. 25, 1990

[54] (22R,23R,24S)-22,23-EPOXY-2α3α-ISO-PROPYLIDENEDIOXY-B-HOMO-7-OXA-5α-STIGMASTAN-6-ONE AND PLANT GROWTH REGULATING METHOD CONTAINING THE SAME

[75] Inventors: Yasuo Kamuro; Toshihito Kakiuchi, both of Tsukuba; Suguru Takatsudo, Joetsu, all of Japan

[73] Assignee: Fujisawa Pharmaceutical Co., Ltd., Osaka, Japan

[21] Appl. No.: 288,563

[22] Filed: Dec. 22, 1988

[30] Foreign Application Priority Data

Dec. 24, 1987 [JP] Japan .................. 62-329228

[51] Int. Cl.$^5$ .............................. A01N 43/30
[52] U.S. Cl. .......................... 71/88; 549/268
[58] Field of Search .................. 549/268; 71/88

[56] References Cited

U.S. PATENT DOCUMENTS 4,453,967  6/1984  Lori ................................. 549/268

FOREIGN PATENT DOCUMENTS 0040517 11/1981 European Pat. Off. ............ 549/268
0231088 12/1984 Japan ............................... 549/268

OTHER PUBLICATIONS

Journal of Agricultural and Biological Chemistry, vol. 48, No. 3, Mar., 1984, pp. 745-752, Tokyo JP; M. Sakakibara et al.: "Short-step syntheses of homodicholide and homodolichosterone" p,. 746, compounds 9,10; p. 748.
Phytochemistry, vol. 25, No. 8, pp. 1787-1799, GB; G. Adam et al.: "Brassinosteroids" Whole Article.

*Primary Examiner*—Glennon H. Hollrah
*Assistant Examiner*—Anilia A. Owens
*Attorney, Agent, or Firm*—Oblon, Spivak, McClelland, Maier & Neustadt

[57] ABSTRACT

This invention relates to (22R,23R,24S)-22,23-epoxy2α3α-isopropylidenedioxy-B-homo-7-oxa-5α-stigmastan-6-one which is of value as a plant growth regulator, a process for preparation thereof and a plant growth regulating composition containing the same.

1 Claim, No Drawings

(22R,23R,24S)-22,23-EPOXY-2α3α-ISOPROPYLI-DENEDIOXY-B-HOMO-7-OXA-5α-STIGMASTAN-6-ONE AND PLANT GROWTH REGULATING METHOD CONTAINING THE SAME

This invention relates to (22R,23R,24S)-22,23-epoxy-2α,3α-isopropylidenedioxy-B-homo-7-oxa-5α-stigmastan-6-one which is of value as a plant growth regulator, a process for preparation thereof and a plant growth regulating composition containing the same.

While a variety of growth regulators for plants are known, brassinolide has recently attracted attention as a new phytohormone and various analogs thereof have been synthesized and studied.

However, while brassinolide and its related compounds have potent plant growth promoting activity, they do not afford stable efficacy under field conditions because of the short duration of action.

This invention provides a brassinolide analog having potent and sustained plant growth promoting activity, a process for preparing the same analog and a plant growth regulating composition containing the same analog as an active ingredient.

The compound of this invention which has accomplished the above-mentioned object has the following chemical structure (I).

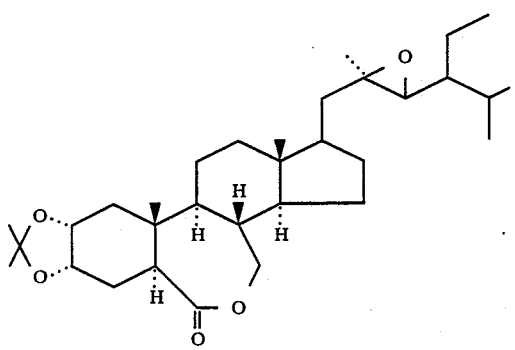

(I)

[(22R,23R,24S)-22,23-epoxy-2α,3α-isopropylidene-dioxy-B-homo-7-oxa-5α-stigmastan-6-one]

The compound (I) of this invention is a novel compound which can be produced by the process shown below by way of reaction formula and described hereinafter.

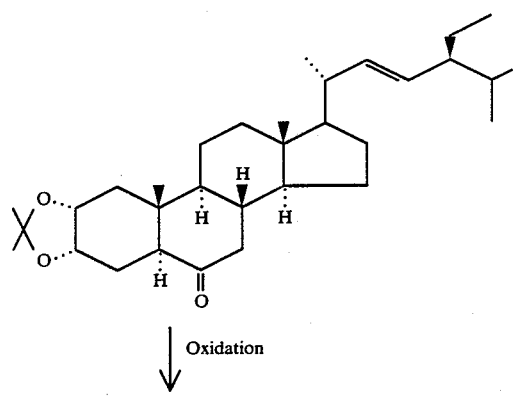

(II)

Oxidation

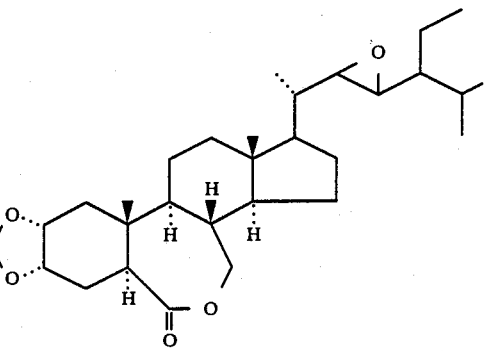

(I)

(22E,24S)-2α,3α-Isopropylidenedioxy-5α-stigmast-22-en-6-one(II), which is used in this reaction, is a known compound described, for example, in Tetrahedron 38, 14, 2099–2109, 1982.

The oxidizing agent to be used in this oxidation reaction includes, among others, organic peroxides such as peroxybenzoic acid, m-chloroperoxybenzoic acid, m-bromoperoxybenzoic acid, performic acid, peracetic acid, chloroperacetic acid, trifluoroperacetic acid and monoperphthalic acid, the sodium or potassium salts thereof, hydrogen peroxide, and mixtures of hydrogen peroxide with said various peroxides.

This reaction is generally carried out in a solvent, such as methylene chloride, ethylene chloride, ethyl acetate, chloroform, dioxane, tetrahydrofuran, benzene, toluene, hexane and so on. Of these solvents, hydrophilic solvents can be used in admixture with water.

The reaction temperature is virtually optional and a suitable temperature can be chosen according to the kinds of starting compound, oxidizing agent and solvent.

Satisfactory results are obtained in many cases when the reaction is conducted in the dark at room temperature using m-chloroperbenzoic acid as the oxidizing agent and methylene chloride or chloroform as the solvent.

The object compound (I) of this invention has potent plant growth promoting activity and is of value as a plant growth regulator. For example, it can be used as a plant growth regulator for promotion of the growth of vegetables such as tomato, egg plant, green pepper, etc., promotion of the growth of flowering plants such as chrysanthemum, carnation, cosmos, etc., promotion of the growth of gramineous crops such as paddy rice, wheat, etc., promotion of the growth of orchard trees such as apple, pear, etc., promotion of the flowers and fruits, improvement of the yields of cereal plants or leguminous plants such as soybean, azuki, peanut, pea, etc., and improvement of the crop yield of potato, for instance.

The method for use of the plant growth regulating composition of this invention depends on the substrate plant but it is generally appropriate to apply the composition to the foliage of the plant. While the optimum application concentration varies with different substrate plants, it is generally as low as about $1 \times 10^{-5}$ ppm to 1 ppm.

To put the plant growth regulator of this invention to use, it can be mixed with various vehicles and made available in the form of dusts, granules, tablets, wettable powder, emulsifiable concentrate or the like according to the intended application. The vehicle may be solid or liquid or a combination thereof. For example, talc, clay, kaolin, diatomaceus earth, calcium carbonate, potassium chlorate, calcium nitrate, nitrocellulose, starch, gum arabic, water, alcohol, benzene, acetone and so on may be mentioned. Furthermore, those auxiliary agents which are generally included in agrochemical formulations, such as adhesives, emulsifying agents, etc. can also be incorporated.

The composition thus obtained is not only useful as such but can be used in admixture with other agrochemicals such as fungicides, insecticides, herbicides, other plant growth regulators, and/or fertilizers.

The following is an example of this invention.

Example 1

To a solution of (22E,24S)-2α,3α-isopropylidenedioxy-5α-stigmast-22-en-6-one (5.0 g) in dichloromethane (80 ml) is added m-chloroperbenzoic acid (5.0 g) and the mixture is stirred in the dark at room temperature for 2 weeks. To the reaction mixture is added calcium hydroxide powder (7.0 g) and the mixture is further stirred at room temperature for 1 hour. The precipitate was separated by filtration and washed with 2 portions of dichloromethane. The filtrate and washings were combined and concentrated, whereby the desired compound is obtained as a crude product. This product is subjected to silica gel chromatography and elution is carried out with hexane-ethyl acetate (5:1→4:1) to give (22R,23R,24S)-22,23-epoxy-2α,3α-isopropylidenedioxy-B-homo-7-oxa-5α-stigmastan-6-one (2.14 g)

IR $\nu_{max}^{CHCl_3}$ (cm$^{-1}$): 2910 (s), 2735 (s), 2325 (w), 1724 (s), 1460 (m), 1405 (w), 1385 (m), 1315 (w), 1260 (m), 1205 (m), 1180 (m), 1160 (w), 1130 (w), 1120 (w), 1060 (m), 1040 (m), 1018 (m), 990 (w)

$^1$H—NMR (200 MHz, CDCl$_3$) δ: 0.71 (3H, s), 0.89 (3H, s), 1.01 (3H, d, J=6.8 Hz), 1.32 (3H, s), 1.52 (3H, s), 2.33 (1H, dd, J=15.5 and 3.5 Hz), 2.49 (2H, m), 2.74 (1H, dd, J=7.1 and 2.2 Hz), 3.29 (1H, dd, J=10.0 and 4.5 Hz), 4.12 (2H, m), 4.38 (1H, m)

FD-MS : m/z 517 (M$^+$+1)

Example 2 (Activity to promote growth of hatsuka radish)

Hatsuka radish sown in early April and having reached a beginning stage of thickening growth and hatsuka radish sown in early May and having reached a 3- to 4-leaf stage were submitted to the test. The test compound was applied in the following manner on May 15.

The test spray solution was prepared by dissolving the test compound in ethanol at a concentration of 100 ppm and diluting the solution with water to a predetermined concentration. To the dilution was added an surfactant (Nitten) at the level of 1:2,000. The test solution thus obtained was sprayed evenly over the whole foliage at the rate of 100 ml/m$^2$.

Twenty days after spraying, 20 roots per group were randomly pulled out and the total root weight was determined.

The results, as percentages (%) in the total root weight against the untreated control group, are shown in the following table.

| Test Compound | Concentration (ppm) | 3 to 4-Leaf stage | Beginning stage of thickening growth |
|---|---|---|---|
| Compound of the invention | $\frac{1}{100}$ | 113 | 115 |
|  | $\frac{1}{1000}$ | 118 | 122 |
| Brassinolide | $\frac{1}{100}$ | 103 | 106 |
|  | $\frac{1}{1000}$ | 104 | 105 |
| Untreated control | — | 100 (346 g/ 20 roots) | 100 (1927 g/ 20 roots) |

Example 3 (Yield increasing activity of corn)

The test plants (Cultivar: Haney Bantam) were cultivated under the standard production attention. The test compound was sprayed at the timing of 5 days before full bloom. The concentration for spraying was $1 \times 10^{-1}$ ppm or $1 \times 10^{-3}$ ppm at a volume of 20 litters per are. 30 Plants of each plot were randomly harvested and total fresh kernel weight per plot was investigated. The results are shown in the following table. The yield are in percent relative to the untreated group.

| | Percentage in weight of total kernel against Control | | |
|---|---|---|---|
| Test compound | $1 \times 10^{-1}$ ppm | $1 \times 10^{-3}$ ppm | 0 (Control) |
| Compound of the invention | 111.5 | 123.7 | 100 |
| Brassinolide | 107.2 | 104.3 | 1350 gr/ 30 plants |

Example 4 (Yield increasing activity of grape)

The test plants (cultivar: Delaware) were cultivated under the standard production attention. The test compound was sprayed at the timing of 7 days before full bloom. The concentration for spraying was $1 \times 10^{-1}$ ppm or $1 \times 10^{-2}$ ppm at a volume of 10 ml per cluster. 30 Clusters of each plot were randomly harvested and total fresh weight per plot was investigated. The results are shown in the following table. The yield are in percent relative to the untreated group.

| | Percentage in weight of total cluster against Control | | |
|---|---|---|---|
| Test Compound | $1 \times 10^{-1}$ ppm | $1 \times 10^{-2}$ ppm | 0 (Control) |
| Compound of the invention | 109.1 | 118.4 | 100 |
| Brassinolide | 106.2 | 105.3 | (4467 gr/ 30 clusters) |

Example 5 (Yield increasing activity of onion)

The test plants (cultivar: Kaizuka) were cultivated under the standard production attention. The test compound was sprayed at the timing of 1 month before harvest. The concentration for spraying was $1 \times 10^{-1}$ ppm or $1 \times 10^{-3}$ ppm at a volume of 10 litters per are. 20 Plants of each plot were randomly harvested and total fresh bulb weight per plot was investigated. The results are shown in the following table. The yield are in percent relative to the untreated group.

| | Percentage in weight of total bulb against Control | | |
|---|---|---|---|
| Test compound | $1 \times 10^{-1}$ ppm | $1 \times 10^{-3}$ ppm | 0 (Control) |
| Compound of the invention | 111.2 | 117.6 | 100 |
| Brassinolide | 102.6 | 104.5 | (2.67 kg/ 20 plants) |

Example 6 (Growth promoting activity of rice)

The seeds of rice (cultivar: Nihonbare) were soaked in the test solution for 20 hours at 25° C. 100 Seeds of each plot were treated with 20 ml of the test solution containing test compound. 100 Seeds were sowed in 15 cm×15 cm×5 cm pot. The test was performed in 2 pots per group. The test plants were cultivated under the green house conditions. The temperature was controlled at 20°–22° C. 30 Days after sowing, total dry weight per each group was investigated. The results are shown in the following table. The dry weight are in percent relative to the untreated group.

| | Percentage in Dry weight against control | | |
|---|---|---|---|
| Test compound | $1 \times 10^{-1}$ ppm | $1 \times 10^{-3}$ ppm | 0 (Control) |
| Compound of the invention | 122.5 | 121.2 | 100 |
| Brassinolide | 104.5 | 110.6 | (3.98 gr/ 2 pots) |

We claim:
1. A method for regulating the growth of plants comprising spraying onto said plant an effective regulating amount of a plant growth regulating composition comprising as an active ingredient, an effective regulating amount of (22R,23R,24S)-22,23-epoxy-2α,3α-isopropylidenedioxy-B-homo-7-oxa-5α-stigmastan-6-one and an agrochemically acceptable vehicle.

* * * * *